US012099037B1

United States Patent
Hu et al.

(10) Patent No.: US 12,099,037 B1
(45) Date of Patent: Sep. 24, 2024

(54) METHOD FOR DETERMINING OPTIMAL CONTENT AND SLENDERNESS RATIO OF FIBER IN COMPRESSION CAST FIBER-REINFORCED CONCRETE

(71) Applicant: Shenzhen University, Shenzhen (CN)

(72) Inventors: Biao Hu, Shenzhen (CN); Feiyang Yi, Shenzhen (CN); Yu Weng, Shenzhen (CN); Yufei Wu, Shenzhen (CN)

(73) Assignee: Shenzhen University, Shenzhen (CN)

( * ) Notice: Subject to any disclaimer, the term of this patent is extended or adjusted under 35 U.S.C. 154(b) by 0 days.

(21) Appl. No.: 18/632,412

(22) Filed: Apr. 11, 2024

(30) Foreign Application Priority Data

Apr. 20, 2023 (CN) .......................... 202310438570.8

(51) Int. Cl.
*G01N 3/10* (2006.01)
*G01N 1/28* (2006.01)
*G01N 33/38* (2006.01)

(52) U.S. Cl.
CPC .............. *G01N 3/10* (2013.01); *G01N 1/286* (2013.01); *G01N 33/383* (2013.01); *G01N 2001/2866* (2013.01)

(58) Field of Classification Search
CPC ........ G01N 3/10; G01N 1/286; G01N 33/383; G01N 2001/2866
See application file for complete search history.

(56) References Cited

U.S. PATENT DOCUMENTS

| | | | | |
|---|---|---|---|---|
| 7,549,320 B2* | 6/2009 | Funkhouser | ......... | G01N 33/383 |
| | | | | 73/865.6 |
| 7,604,159 B2* | 10/2009 | Novak | ..................... | E04C 5/073 |
| | | | | 235/375 |
| 9,664,648 B2* | 5/2017 | Bois | ..................... | G01N 29/024 |
| 11,300,557 B1* | 4/2022 | Bi | ............................. | G01L 5/00 |
| 11,630,097 B2* | 4/2023 | Chen | ........................ | G01N 1/38 |
| | | | | 73/803 |

(Continued)

OTHER PUBLICATIONS

FZ/T 52024-2012, Polyethylene/polypropylene (PE/PP) bicomponent staple fiber, Jiangsu Jiangnan High Fiber Co., Ltd., Issue Date Dec. 28, 2012, 11 pages.

(Continued)

*Primary Examiner* — Freddie Kirkland, III
(74) *Attorney, Agent, or Firm* — Blueshift IP; Robert Plotkin (57) ABSTRACT

A method for determining an optimal fiber content and fiber slenderness ratio in compression-cast fiber-reinforced concrete (CCFRC). The method includes: step 1, determining an optimal range of pressure of CCFRC with a mix proportion; step 2, applying optimal compressive stress to a fiber-reinforced concrete mixture, and performing a uniaxial compression test after demolding and curing; step 3, keeping the slenderness ratio of the fiber in step 1 and the optimal compressive stress in step 2 unchanged, decreasing or increasing content of the fiber, and repeating step 2 to obtain a mechanical property of CCFRC with different content of the fiber; and step 4, keeping the content of the fiber in step 1 and the optimal compressive stress in step 2 unchanged, decreasing or increasing a slenderness ratio of the fiber, and repeating step 2 to obtain a mechanical property of CCFRC with a different slenderness ratio of the fiber.

5 Claims, 8 Drawing Sheets

(56) References Cited

U.S. PATENT DOCUMENTS

| | | | | |
|---|---|---|---|---|
| 11,667,054 B2* | 6/2023 | Tregger | .................. | B28C 5/422 |
| | | | | 702/1 |
| 11,719,620 B2* | 8/2023 | Mukhtar | .................. | G01N 3/04 |
| | | | | 73/842 |
| 11,883,982 B2* | 1/2024 | Wu | .......................... | B28B 3/022 |

OTHER PUBLICATIONS

GB/T 14684-2011, Sand for construction, Shanghai Building Research Institute (Group) Co., Ltd., et al., Issue Date Jun. 16, 2011, 34 pages.

GB/T 14685-2011, Pebble and crushed stone for construction, China Sand and Stone Association, et al., 2011, Issue Date Jun. 16, 2011, 33 pages.

GB/T 26745-2021, Basalt fiber composites for civil engineering structures, Zhejiang Shijin Basalt Fiber Co. Ltd., Issue Date Aug. 20, 2021, 13 pages.

GB/T 50081-2019, Standard for Test Methods of Physical and Mechanical Properties of Concrete, China Institute of Builing Research Co., Ltd., 2019, 113 pages.

JP/T 472-2015, Stell fiber reinforced concrete, North China University of Water Resources and Hydropower, Issue Date Mar. 4, 2015, 33 pages.

\* cited by examiner

METHOD FOR DETERMINING OPTIMAL CONTENT AND SLENDERNESS RATIO OF FIBER IN COMPRESSION CAST FIBER-REINFORCED CONCRETE

CROSS-REFERENCE TO RELATED APPLICATION

This patent application claims the benefit and priority of Chinese Patent Application No. 2023104385708, filed with the China National Intellectual Property Administration on Apr. 20, 2023, the disclosure of which is incorporated by reference herein in its entirety as part of the present application.

TECHNICAL FIELD

The present disclosure relates to the field of concrete casting technologies, and in particular to a method for determining an optimal content and slenderness ratio of fiber in compression-cast fiber-reinforced concrete (CCFRC).

BACKGROUND

After being developed in the 19th century, the concrete material is continuously developed and innovated, and gradually becomes the most widely used construction material. Due to its high strength, low costs, durability, and good working performance, the concrete material is widely used in five major engineering fields, namely, civil engineering, water conservancy engineering, transportation, marine and harbor construction engineering, and aerospace engineering. While concrete material is continuously developed to a high strength, high performance, multifunction, and intelligence, it can be foreseen that in a quite long time in the future, concrete material will still indispensable in the construction field. However, the concrete material has natural defects such as larger dead weight, high brittleness, easy cracking and low tensile strength. Besides, the impact of the environment on the performance, especially durability, of the concrete material is not considered during the structural design of the concrete. In this regard, the concrete structure is usually prone to premature failures. As a result, the popularization and application of the concrete material are limited to some extent. Therefore, to reduce the consumption of mineral resources such as natural aggregates, economic losses, and casualties, and to prolong the service life of the concrete structure, improvement in the performance of the concrete material has become a trend.

At present, there are three conventional methods for improving the performance of concrete material. The first method is to optimize the basic component, that is, to change a water-cement ratio, the nature of cement and aggregate, gradation of aggregate in the process of concrete preparation, to improve the performance of the concrete material. However, this method cannot provide a desirable improvement effect on the performance of the concrete material, might have a bad effect in the working performance of the concrete, has a special requirement for a service environment, and requires a large number of mineral resources such as energy and natural aggregate. A second method is to add additives for compounding, that is, to add additives or various fibers such as fly ash, ground granulated blast furnace slag, calcined clay, water-reducing agent, early strength agent, and air-entraining agent in the process of concrete preparation, without affecting the working performance of the concrete, to improve the performance of the concrete, for example, compression resistance, tensile resistance, shear resistance, bending resistance, durability, and fatigue resistance. However, at present, the solution of adding additives and fibers leads to a significant increase in production costs. The third method is an ordinary compression casting method, that is, a specific compressive stress is applied to a fresh concrete mixture for compression cast, to significantly improve the compressive strength and a modulus of elasticity of the concrete. Although existing research indicates that the cost of compression casting concrete is comparable to that of an ordinary concrete product while improving the performance of the concrete, strength improvement due to compression casting is associated with higher brittleness. Therefore, there is an urgent need for a method to improve the brittleness of compression-cast concrete without degrading the mechanical properties of the concrete.

SUMMARY

An objective of the present disclosure is to provide a method for determining a fiber content and fiber slenderness ratio in compression-cast fiber-reinforced concrete (CCFRC), to resolve the foregoing problems in a conventional technology. The content and slenderness ratio of the fiber in CCFRC may be optimally adjusted, to determine ranges of the optimal content and slenderness ratio of the fiber. In addition, when a designed compressive strength of the CCFRC is ensured, the toughness of the CCFRC can be improved to the greatest extent.

To achieve the foregoing objective, the present disclosure provides the following solutions:

The present disclosure provides a method of determining an optimal fiber content and fiber slenderness ratio in CCFRC. The method includes the following steps:

step 1, selecting and fixing a fiber content and fiber slenderness ratio that meets a specification; setting a first compressive stress, a pressurization amount, and a pressurizing time; pouring fresh concrete into a mold, and controlling, based on the first compressive stress and the pressurizing time, a pressurizing structure to apply a pressure on the concrete, to obtain a first average compressive strength of the concrete; determining a second compressive stress of the concrete based on the pressurization amount and the first compressive stress, pouring the fresh concrete into the mold, and controlling, based on the second compressive stress and the pressurizing time, the pressurizing structure to apply a pressure to the concrete, to obtain a second average compressive strength of the concrete, and by analogy to obtain an $N^{th}$ average compressive strength, where in the process, a compressive stress that is correspondingly applied each time is gradually increased based on the pressurization amount, and when the $N^{th}$ average compressive strength is less than an $(N-1)^{th}$ average compressive strength, stopping increasing the compressive stress, drawing a relationship curve of a compressive strength and the compressive stress of the CCFRC, and determining an optimal range of the compressive stress of the CCFRC;

step 2, taking a fixed value within the optimal range of the compressive stress of the CCFRC in step 1 as an acceptable optimal compressive stress; applying the optimal compressive stress to the fresh concrete by compression casting, maintaining the optimal compressive stress for a specific period of time, and performing a uniaxial compression test after demolding and curing for a preset number of days, to obtain a mechanical property of the CCFRC under the optimal compressive stress;

step 3, keeping the slenderness ratio of the fiber in step 1 and the optimal compressive stress in step 2 unchanged, decreasing or increasing the content of the fiber, keeping a content of another material unchanged, repeating step 2 to obtain a mechanical property of CCFRC with different content of the fiber under the optimal compressive stress, drawing a relationship curve of average toughness and the content of the fiber in the CCFRC, to statistically determine an optimal range of the content of the fiber;

step 4, keeping the content of the fiber in step 1 and the optimal compressive stress in step 2 unchanged, decreasing or increasing the slenderness ratio of the fiber, keeping the content of another material unchanged, and repeating step 2 to obtain a mechanical property of CCFRC with a different slenderness ratio under the optimal compressive stress, drawing a relationship curve of toughness and the slenderness ratio of the fiber in the CCFRC, to statistically determine an optimal range of the slenderness ratio of the fiber.

Specifically, step 1 includes:

first step, in the premise of meeting a national specification and standard, selecting and fixing a content and slenderness ratio of the fiber, determining a mix proportion of the CCFRC, and selecting a raw material required for the preparation of the CCFRC, including a coarse aggregate, a fine aggregate, fiber, and cement;

second step, in the premise of meeting a loading capacity of current compression casting equipment, setting an initial pre-compressive stress $S_x=0$, an initial step $x=0$, and an increment $\Delta S$ of the compressive stress applied each time;

third step, preparing the CCFRC mixture, pouring the CCFRC mixture into the mold, pressurizing the CCFRC mixture to a preset compressive stress by the pressurizing structure, removing an outer mold after maintaining the preset compressive stress for a first preset time, removing an inner mold after a second preset time, performing the uniaxial compression test on a specimen after standard curing of the CCFRC mixture for a third preset time, calculating an average compressive strength of three specimens in a same group, and denoting the average compressive strength as $f_x$; if $f_x<f_{x-1}$, performing the fifth step; or if $f_x \geq f_{x-1}$, performing the fourth step;

fourth step, increasing the pre-compressive stress to $S_x+\Delta S_x$, $x=x+1$, and performing second step;

fifth step, obtaining a relationship curve of an average compressive strength f and pre-applied compressive stress $S_x$ of the CCFRC, where $x=0, 1, 2, \ldots, n$, determining a minimum value and a maximum value within the optimal range of the compressive stress based on the curve, where $f_o=f_{co}$ represents a compressive strength of ordinary concrete, a compressive strength $f_{ct}$ represents a designed minimum compressive strength of the CCFRC, when a compressive strength $f_a$ is greater than and closest to a designed compressive strength $f_{ct}$, a compressive stress $S_a$ corresponding to the compressive strength $f_a$ is the minimum compressive stress in the optimal range, a compressive stress strength $S_h$ corresponding to a compressive strength $f_h$ at a highest point is the maximum compressive stress in the optimal range, and when determining the selected content and slenderness ratio of the fiber in the first step, determining the optimal range of the compressive stress of the CCFRC;

sixth step, repeating the second step to the fifth step with the same concrete material and mix proportion, in the premise that the content and slenderness ratio of the fiber are the same as those in the first step, if the optimal range of the compressive stress of the CCFRC is the same as that in the fifth step, determining a result, or if the optimum compressive stress range for the CCFRC is not the same as in the fifth step, repeat the second step to the sixth step until repeatable results are obtained.

Specifically, the step of determining an optimal range of the content of the fiber includes:

seventh step, based on the optimal range of the compressive stress determined in the sixth step, selecting and fixing an integer compressive stress $S_k$ within the range as the acceptable optimal compressive stress;

eighth step, while the fixed slenderness ratio of the fiber is the same as that in the first step and $i=0$, setting an initial content of the fiber $P_i=0\%$, and determining an addition increment $\Delta P$ of the fiber;

ninth step, preparing the CCFRC mixture, pouring the CCFRC mixture into the mold, pressurizing the CCFRC mixture by a pressurizing structure to $S_k$, removing an outer mold after maintaining the preset compressive stress for a first preset time, removing an inner mold after a second preset time, performing the uniaxial compression test on a specimen after standard curing of the CCFRC mixture for a third preset time, calculating an average toughness of three specimens in a same group, and denoting the average toughness as $T_i$, if $T_i<T_{i-1}$, performing the eleventh step, or if $T_i \geq T_{i-1}$, performing the tenth step;

tenth step, increasing the content of the fiber to $P_i+\Delta P$, $i=i+1$, and performing eighth step;

eleventh step, in the premise that the slenderness ratio of the fiber is the same as that in the first step, obtaining a relationship curve of average toughness $T_i$ and the content of the fiber in the CCFRC where $i=0, 1, 2, \ldots, n$, determining a minimum value and a maximum value within an optimal range of the content of the fiber based on the curve, where $T_o=T_{co}$ represents toughness of ordinary concrete, and toughness $T_{ct}$ represents designed minimum toughness of the CCFRC, when toughness $T_g$ is greater than and closest to a designed toughness $T_{ct}$, a content $P_g$ of the fiber corresponding to the toughness $T_g$ is the minimum content within the optimal range, and a content $P_m$ of the fiber corresponding to toughness $T_m$ at the highest point of the curve is the maximum content within the optimal range; and twelfth step, repeating the eighth step to the eleventh step with the same concrete material and mix proportion, if the minimum content and the maximum content of the fiber that are within the optimal range and that are obtained based on the relationship curve of average toughness and the content of the fiber in the CCFRC are the same as those in the eleventh step, determining a result, or if the minimum content and the maximum content of the fiber that are within the optimal range and that are obtained based on the relationship curve of average toughness and the content of the fiber in the CCFRC are not the same as that in the eleventh step, repeating the eighth step to the twelfth step until that a reproducible result is obtained.

Specifically, the step of determining an optimal range of the slenderness ratio of the fiber includes:

seventh step, on the basis of the optimal range of the compressive stress determined in the sixth step, selecting and fixing the integer compressive stress $S_k$ within the range as the optimal compressive stress;

eighth step, while the content of the fiber is the same as that in the first step and $\lambda_e=0$, setting an initial slenderness ratio of the fiber $\lambda_e=0$, and setting an increment $\Delta\lambda=(l_e-l_{e-1})/d$, where l represents a length of the fiber, and d represents a diameter of the fiber;

ninth step, preparing the CCFRC mixture, pouring the CCFRC mixture into the mold, pressurizing the CCFRC mixture by a pressurizing structure to $S_k$, and removing an outer mold after maintaining the preset compressive stress for a first preset time, removing an inner mold after a second preset time, performing the uniaxial compression test on a specimen after standard curing of the CCFRC mixture for a third preset time, calculating an average toughness of three specimens in a same group, and denoting the average toughness as $T_e$, if $T_e<T_{e-1}$, performing the eleventh step, or if $T_e \geq T_{e-1}$, performing the tenth step;

tenth step, increasing the slenderness ratio of the fiber to $\lambda_e+\Delta\lambda$, e=e+1, and performing the eighth step;

eleventh step, in the premise that the content of the fiber is the same as that in the first step, obtaining a relationship curve of average toughness $T_e$ and the slenderness ratio of the fiber in the CCFRC, where e=0, 1, 2, . . . , n, determining a minimum value and a maximum value within the optimal range of the slenderness ratio of the fiber based on the curve, where $T_o=T_{co}$ represents toughness of ordinary concrete, and toughness $T_{ct}$ represents designed minimum toughness of the CCFRC, when toughness $T_j$ is greater than and closest to a designed toughness $T_{ct}$, a slenderness ratio $\lambda_j$ of the fiber corresponding to the toughness $T_j$ is the minimum slenderness ratio within the optimal range, and a slenderness ratio $\lambda_w$ corresponding to toughness $T_w$ at the highest point of the curve is the maximum slenderness ratio within the optimal range;

twelfth step, repeating the eighth step to the eleventh step with the same concrete material and mix proportion, if the minimum value and the maximum value of the slenderness ratio of the fiber that are within the optimal range and that are obtained based on the relationship curve of average toughness and the content of the fiber in the CCFRC are the same as those in the eleventh step, determining a result, or if the minimum value and the maximum value of the slenderness ratio of the fiber that are within the optimal range and that are obtained based on the relationship curve of average toughness and a content of the fiber in the CCFRC are not the same as those in the eleventh step, repeating the eighth step to the twelfth step until that a reproducible result is obtained; and finally determining ranges of an optimal content and slenderness ratio of the fiber to be added to the CCFRC under the optimal compressive stress.

Specifically, the increment $\Delta S$ of the compressive stress applied each time is 1 MPa to 2 MPa.

Specifically, after the specimen is taken out from a curing room, first, an end part that is compressed by a jack head is ground by using a grinding machine, to enable a surface to be flat and smooth, second, the uniaxial compression test is performed on the specimen by using a compression test apparatus, where a loading system is to perform force control first and then perform displacement control, with a loading rate of the force control of 1 KN/s, and when a force reaches 5 KN, displacement control is performed at a loading rate of the displacement control of 0.3 mm/min; in a testing process, for the longitudinal strain of the specimen, a deformation of the specimen needs to be measured by using a measuring system with a measuring length of 185 mm; and for the transverse strain of the specimen, measurement needs to be performed by using four strain gauges that are horizontally arranged with a length of 50AA, and a data acquisition rate is 1 Hz.

Specifically, when an added fiber is coarse fiber, the addition increment of the fiber is $\Delta P=0.50\%$, or when an added fiber is fine fiber, the addition increment of the fiber is $\Delta P=0.05\%$.

Specifically, after the compressive stress is stabilized, the compression amount is maintained, pressurization is continuously performed for 2 minutes, the outer mold is immediately removed, the inner mold is removed after 24 hours, the specimen is taken out from the curing room after standard curing for 28 days, and the uniaxial compression test is performed.

Compared with conventional technology, the present disclosure has the following technical effect:

According to the present disclosure, the mechanical property of ordinary fiber-reinforced concrete is greatly improved by compression casting, to more widely use the CCFRC in the engineering field. According to the present disclosure, using compression casting, compression casting can maintain a price comparable to that of an ordinary fiber-reinforced concrete product while improving the performance of the CCFRC, to achieve a good effect of low carbon emissions and low costs. According to the present disclosure, while significantly improving the mechanical property of the CCFRC, the compression casting reduces the overall porosity of the CCFRC, improves the transition zone of an interface between the fiber and a mortar matrix, and improves the durability of the CCFRC. According to the present disclosure, the efficiency of improving the performance of the CCFRC is particularly high, with a processing time of 2 minutes to 8 minutes. According to the present disclosure, optimal ranges of the content and slenderness ratio of the fiber added to the CCFRC can be obtained. Therefore, when the CCFRC is prepared, by adding fiber within the ranges of the optimal content and slenderness ratio, a designed compressive strength of the CCFRC can be ensured. In addition, the toughness of the CCFRC can be improved to the greatest extent, and a good toughening effect is implemented. The technology in the present disclosure is a physical technology, without additives and without replacing a component of the concrete. Therefore, high-performance concrete with a high strength and high toughness can be produced. The technology can be applied to steel fiber-reinforced concrete, polypropylene fiber-reinforced concrete, basalt fiber-reinforced concrete, or any other fiber-reinforced concrete.

BRIEF DESCRIPTION OF THE DRAWINGS

To describe the technical solutions in embodiments of the present disclosure or in the conventional technology more clearly, the following briefly describes the accompanying drawings for describing embodiments. It is clear that the accompanying drawings in the following description show merely some embodiments of the present invention, and a person of ordinary skill in the art may still derive other drawings from these accompanying drawings without creative efforts.

Figure 1:
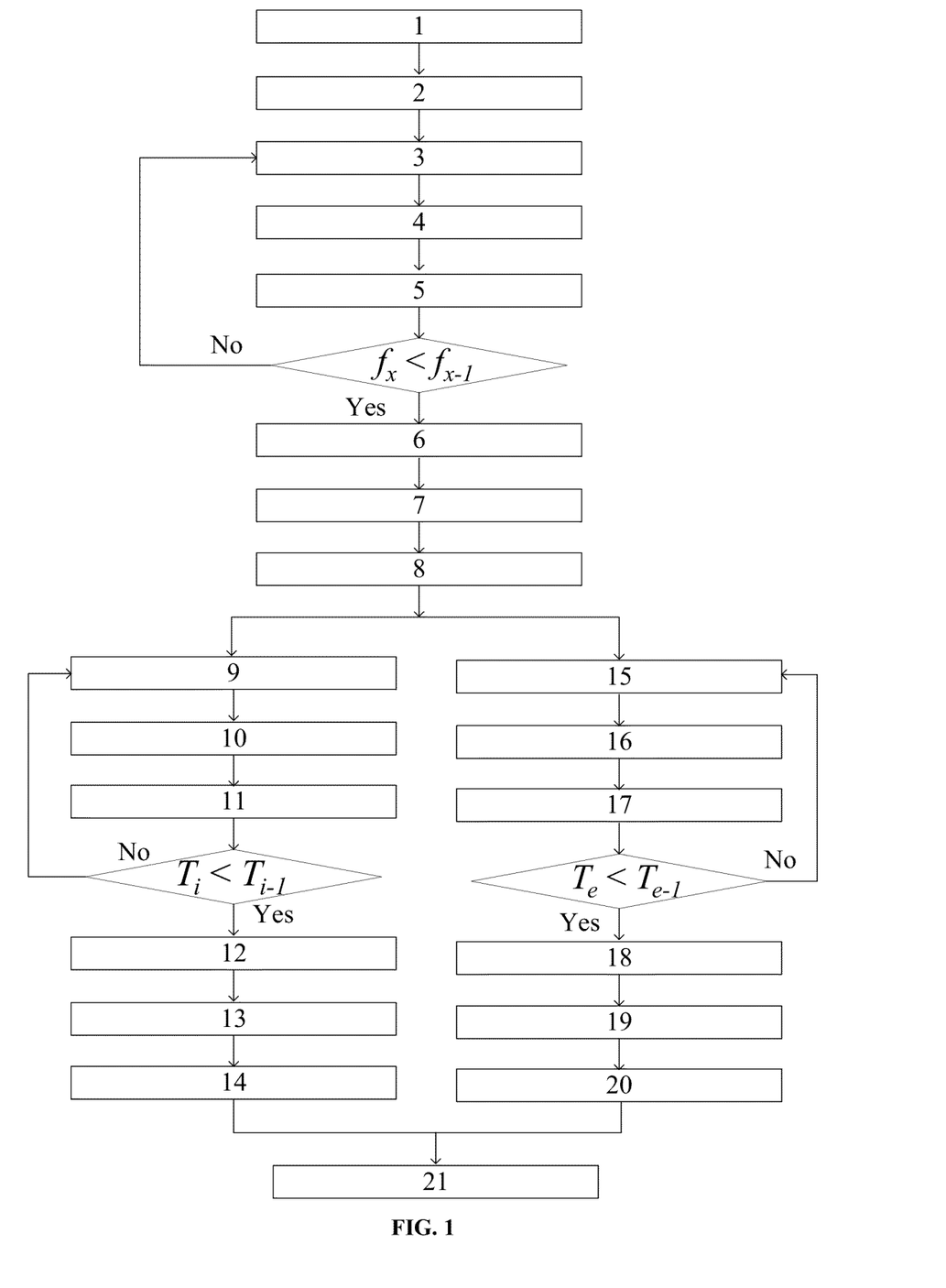
FIG. 1 is a schematic flowchart of a method for determining an optimal content and slenderness ratio of fiber in CCFRC according to the present disclosure.

REFERENCE NUMERALS IN FIG. 1

1—Prepare materials for fiber-reinforced concrete
2—Meet a mix proportion specified in a specification
3—Set an initial step x=0, select and fix a content and slenderness ratio of a fiber that meets a specification requirement, and set an initial pre-compressive stress $S_x=0$ and an increment $\Delta S=1-2$ MPa
4—Apply the compressive stress $S_x$ and maintain for 2 minutes
5—For each compressive stress $S_x$, measure an average compressive strength $f_x$ of compression-cast fiber-reinforced concrete
6—Draw a relationship curve of a compressive strength $f_x$ and a compressive stress S (x=0–n) of the CCFRC, where when a compressive strength $f_a$ is greater than and closest to a designed $f_{ct}$, a compressive stress $S_a$ corresponding to the compressive strength $f_a$ is a minimum compressive stress within an optimal range, and a compressive stress $S_h$ corresponding to a compressive strength $f_h$ at a highest point of the curve is a maximum compressive stress within in the optimal range
7—For a same material and mix proportion, repeat the foregoing steps until that $S_a$ and $S_h$ convergences (within an allowable range of an error) are obtained
8—On the basis of optimal ranges of the content and slenderness ratio of the fiber, select and fix a compressive stress $S_k$ within the optimal range of the compressive stress as an acceptance optimal compressive stress
9—Fix the selected slenderness ratio of the fiber, and when i=0, set an initial content $P_i=0\%$ of the fiber and an increment $\Delta P=0.50\%$ (applicable to a coarse fiber, for example, a steel fiber) or 0.05% (applicable to a fine fiber, for example, a polypropylene fiber/basalt fiber), $P_{i+1}=P_i+\Delta P$
10—Apply the compressive stress $S_k$, and maintain for 2 minutes
11—For each content $P_i$ of the fiber, measure the average toughness $T_i$ of the compression-cast fiber-reinforced concrete
12—Draw a relationship curve of toughness $T_i$ and a content P of the fiber of the CCFRC (i=0–n), where when toughness $T_g$ is greater than and closest to a designed $T_{ct}$, a content $P_g$ of the fiber corresponding to the toughness $T_g$ is a minimum content within an optimal range, and a content $P_m$ of a fiber corresponding to toughness $T_m$ at a highest point of the curve is a maximum content of the fiber within the optimal range
13—For the same material and mix proportion, repeat the foregoing steps until $P_g$ and $P_m$ convergences (within an allowable range of an error) are obtained
14—On the basis of the optimal range of the content of the fiber under the optimal compressive stress $S_k$ determined in the foregoing steps, select a content $P_k$ between the maximum value and the minimum value of the content as an acceptance optimal content
15—Fix the selected content of the fiber, and when e=0, set an initial slenderness ratio $\lambda_e=0$ and an increment $\Delta\lambda=(l_e-l_{e-1})/d$, $\lambda_{e+1}=\lambda_e+\Delta\lambda$
16—Apply the compressive stress $S_k$, and maintain for 2 minutes
17—For each slenderness ratio λe of the fiber, measure the average toughness Te of the compression-cast fiber-reinforced concrete
18—Draw a relationship curve of toughness $T_e$ and a slenderness ratio λ of the fiber of the CCFRC (e=0–n), where when toughness $T_j$ is greater than and closest to a designed $T_{ct}$, a slenderness ratio $\lambda_j$ of a fiber corresponding to the toughness $T_j$ is a minimum slenderness ratio within an optimal range, and $\lambda_w$ corresponding to toughness $T_w$ at a highest point of the curve is a maximum slenderness ratio within the optimal range
19—For the same material and mix proportion, repeat the foregoing steps until that $\lambda_j$ and $\lambda_w$ convergences (within an allowable range of an error) are obtained
20—On the basis of the optimal range of the slenderness ratio of the fiber under the optimal compressive stress $S_k$, select an integer slenderness ratio $\lambda_k$ between the maximum value and the minimum value of the slenderness ratio as an acceptance optimal slenderness ratio
21—Obtain an optimal content and slenderness ratio of a fiber added to the compression-cast fiber-reinforced concrete.

DETAILED DESCRIPTION OF THE EMBODIMENTS

The following clearly and completely describes the technical solutions in embodiments of the present invention with reference to the accompanying drawings in embodiments of the present invention. It is clear that the described embodiments are merely a part rather than all of the embodiments of the present invention. All other embodiments obtained by a person of ordinary skill in the art based on embodiments of the present invention without creative efforts shall fall within the protection scope of the present invention.

An objective of the present disclosure is to provide a method for determining an optimal fiber content and fiber slenderness ratio in CCFRC, to resolve the foregoing problems in the prior art. By optimally adjusting a fiber content and fiber slenderness ratio added to the CCFRC, ranges of the optimal content and slenderness ratio of the fiber are obtained. In addition, while the designed compressive strength of the CCFRC is ensured, the toughness of the CCFRC can be improved to the greatest extent.

To make the above-mentioned objective, features, and advantages of the present disclosure clearer and more comprehensible, the present disclosure will be further described in detail below in conjunction with the accompanying drawings and specific embodiments.

The present disclosure provides a method for determining an optimal fiber content and fiber slenderness ratio in CCFRC. The method includes the following steps.

Step 1: For a mix proportion (including cement (C), water (W), coarse aggregate (CA), fine aggregate (FA), and fiber (FB)) of fiber-reinforced concrete, apply optimal compressive stress (for example, 15 MPa) to the fresh concrete by compression casting, maintain a compression amount, continuously pressurize for 2 minutes, and perform a uniaxial compression test after demolding and curing for 28 days, to obtain a mechanical property of the CCFRC under the optimal compressive stress. A method of determining an optimal range of the compressive stress includes: Determining designed compressive strength information and pressurization information of the concrete, where the pressurization information includes a pressurization amount and a pressurizing time; determining a first compressive stress for the concrete based on the pressurization information, pouring fresh concrete into a mold based on the first compressive stress and the pressurizing time, and controlling a pressurizing structure to apply a pressure on the concrete, to obtain a first average compressive strength of the concrete; and determining a second compressive stress for the concrete based on the pressurization amount and the first compressive stress, pouring the fresh concrete into the mold, and controlling the pressurizing structure to apply a pressure on the concrete based on the second compressive stress, the pressurizing time, and an average compressive strength information, to obtain a second average compressive strength of the concrete, and by analogy to obtain a third average compressive strength and a fourth average compressive strength, until an $N^{th}$ average compressive strength is obtained, where in the process, a compressive stress that is correspondingly applied each time is gradually increased based on the pressurization amount, and when the $N^{th}$ average compressive strength is less than an $(N-1)^{th}$ average compressive strength, stopping increasing the compressive stress, drawing a relationship curve of a compressive strength and the compressive stress of the CCFRC, and determining an optimal pressure range of the CCFRC.

Step 2: Select a fixed value within the optimal range of the compressive stress of the CCFRC in step 1 as an acceptable optimal compressive stress, applying the optimal compressive stress to the fresh concrete by the compression casting, and maintain the optimal compressive stress for a specific period of time, and perform a uniaxial compression test after demolding and curing for a preset number of days, to obtain a mechanical property of the CCFRC under the optimal compressive stress.

Step 3: Keep the slenderness ratio of the fiber in step 1 and the optimal compressive stress in step 2 unchanged, decrease or increase the content of FB, keep contents of C, W, CA, and FA unchanged, and repeat step 2 to obtain a mechanical property of CCFRC with a different content of the fiber. Continue to decrease or increase the content of the FB, keep the contents of C, W, CA, and FA unchanged until the content is reduced to zero or increased to a value that seriously affects the performance of the concrete, collate, and analyze test data of a test sample, and draw a relationship curve of average toughness and the content of the fiber in the CCFRC, to statistically determine the optimal range of the content of the fiber.

Step 4: Finally, keep the content of the fiber in step 1 and the optimal compressive stress in step 2 unchanged, decrease or increase the slenderness ratio of the FB, keep the contents of C, W, CA, and FA unchanged, and repeat step 2 to obtain a mechanical property of CCFRC with a different slenderness ratio. Continue to decrease or increase the slenderness ratio of the FB, keep the contents of C, W, CA, and FA unchanged until the slenderness ratio is reduced to zero or increased to a value that fibers are seriously agglomerated, collate and analyze test data of a test sample, and draw a relationship curve of average toughness and the slenderness ratio of the fiber in the CCFRC, to statistically determine the optimal range of the slenderness ratio of the fiber.

The CCFRC by the method provided in the present disclosure can significantly improve various mechanical properties of the CCFRC, for example, for C30 concrete, compared with compression-cast ordinary concrete at an optimal pressure, a compressive strength of compression cast PP fiber-reinforced concrete can be improved by 8.53% and toughness can be improved by 13.63%.

Compared with a method for optimizing a basic component, in the technology provided in the present disclosure, while the toughness of fiber-reinforced concrete with a mix proportion is improved or kept unchanged, energy consumption is reduced. Compared with a method for adding additives for compounding, in the method provided in the present disclosure, a mineral admixture and a chemical additive need not be added. The method is a physical compression method. Therefore, when the toughness of the concrete is improved, the price of the concrete can be maintained at a price comparable to that of an ordinary fiber-reinforced concrete product. Compared to an ordinary compression casting method, in the method provided in the present disclosure, the fiber is added by a physical method. Therefore, while the strength of the concrete is improved, the increase in brittleness of the CCFRC caused by an improved strength is resolved. The present disclosure applies to any fiber-reinforced concrete, including steel fiber-reinforced concrete, polypropylene fiber-recycled concrete, basalt fiber-reinforced concrete, steel fiber-recycled aggregate concrete, polypropylene fiber-recycled aggregate concrete, and basalt fiber-recycled aggregate concrete, with strong applicability, simple operations, and uniform processes. The present disclosure applies to a precast concrete member in any shape, including a cylinder, a prism, a square, a concrete block, a beam, a slab, and a column.

Embodiment 1

With reference to FIG. 1, this embodiment is a further improvement made on the foregoing technical solutions. An operation method in this embodiment includes a step of determining an optimal compressive stress for CCFRC, a step of determining an optimal range of fiber content, and a step of determining an optimal range of a fiber slenderness ratio.

The step of determining an optimal compressive stress for CCFRC includes the following steps.

First step: According to *Standard for Test Methods of Concrete Physical and Mechanical Properties* GB/T 50081-2019, *Pebble and Crushed Stone for Construction* GB/T 14685-2011, *Sand for Construction* GB/T 14684-2011, *Steel Fiber Reinforced Concrete* JG/T 472-2015, *Polyethylene Polypropylene(PE/PP) Bicomponent Staple Fiber* FZ/T 52024-2012, and *Basalt Fiber Composites for Civil Engineering Structures* GB/T 26745-2021, select and fix a fiber content and fiber slenderness ratio, for example, a polypropylene fiber with a content of 0.15% and a slenderness ratio of 313, determine a mix proportion of the CCFRC, select and prepare raw materials for preparing of the CCFRC, such as coarse aggregate, fine aggregate, cement, and a fiber.

Second step: In the premise of meeting a current loading capacity of compression casting equipment, set an initial pre-compressive stress $S_x=0$, an initial step x=0, and increment $\Delta S$ 1-2 MPa of compressive stress applied each time.

Third step: Prepare CCFRC, first, evenly pour the mixed fiber-reinforced concrete three times into a special steel mold with a pre-designed height, continuously vibrate the concrete poured each time by an insert type vibrating bar with a power of 3,000 watts for 5 times to 8 times (several times of vibration are related to the mix proportion of the concrete, the content of the fiber, the slenderness ratio of the fiber, and a shape of the mold), pour next concrete until that three vibrations are completed, perform centering and leveling on the mold filled with concrete and a loading device, to enable a circular pressure head is vertically centered with a position of a cylinder mold, and apply downward pressure by using a jack. If the centering and leveling are not accurate, a press bar is easy to bend, resulting in damage to an instrument and equipment.

Fourth step: Immediately pressurize the fresh concrete in third step to the preset compressive stress $S_x$, after the compressive stress is stabilized, maintain a compression amount, continuously pressurize for about 2 minutes, stop pressurizing, immediately removing an outer mold, remove an inner mold after waiting for 24 hours, taking out a specimen from a curing room after standard curing for 28 days, and perform the uniaxial compression test on the specimen by using a 3,000 KN MTS compression test apparatus. In a test process, a measurement system is used to measure an axial deformation of the specimen. The measurement system includes four linear variable displacement transducers (LVDTs) that are at right angles to each other and fastened on an aluminum frame and has a measuring length of 185 mm. In addition, four horizontal strain gauges are used to measure the transverse strain of the specimen. To record an applied load and deformation well, all specimens in the present disclosure are tested in a loading mode of performing force control and then performing displacement control. A loading system of the mode is with a loading rate for force control is 1 KN/s, and when a force reaches 5 KN, perform displacement control, with a loading rate of the displacement control of 0.3 mm/min and a data acquisition rate of 1 Hz. Finally, calculate the average compressive strength of three specimens in the same group, and denote the average compressive strength as $f_x$. If $f_x < f_{x-1}$, perform sixth step, or if $f_x \geq f_{x-1}$, perform fifth step.

Fifth step: Increase the pre-compressive stress to $S_x+\Delta S_x$, x=x+1, and perform second step.

Figure 2:
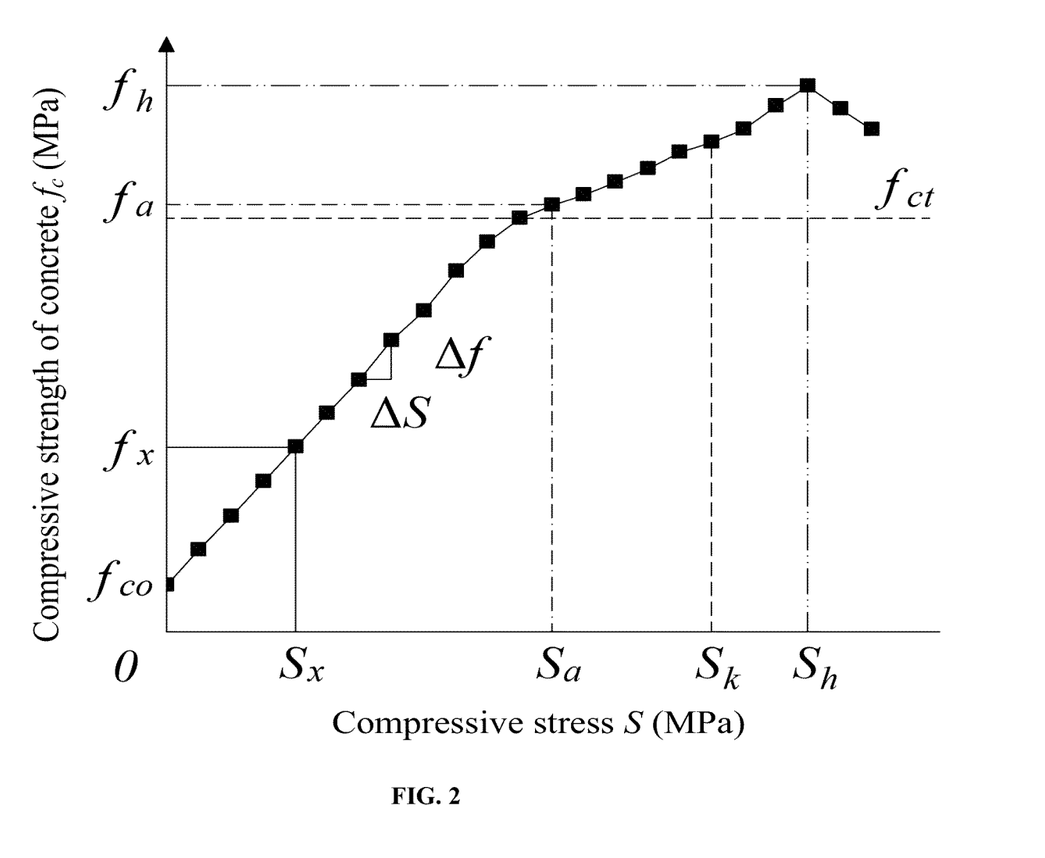
FIG. 2 is a schematic diagram of a relationship between compressive stress and an average strength of CCFRC.

Sixth step: Draw a relationship curve of a compressive strength $f_x$ and a compressive stress S(x=0, 1, 2, ..., n). When a compressive strength $f_a$ is greater than and closest to a designed $f_{cr}$, a compressive stress $S_a$ corresponding to the compressive strength $f_a$ is the minimum compressive stress within the optimal range, and a compressive stress $S_h$ corresponding to a compressive strength $f_h$ at the highest point of the curve is the maximum compressive stress within in the optimal range, as shown in FIG. 2.

Seventh step: Perform one to two series of experiments with the same concrete material and mix proportion, repeat the second step to the sixth step until that $S_a$ and $S_h$ convergences (within an allowable range of an error) are obtained, in the premise that contents and slenderness ratios of the fibers are the same, if a minimum optimal compressive stress result and a maximum optimal compressive stress result are the same as those in the sixth step, determine the results, or if a minimum optimal compressive stress result and a maximum optimal compressive stress result are not the same as those in the sixth step, repeat second step to seventh step until that a repeatable result is obtained.

The step of determining an optimal range of fiber content in this embodiment includes the following steps.

Eighth step: On the basis of the optimal ranges of the fiber content determined in second step to seventh step, select and fix an integer pressure stress $S_k$ within the optimal range of the compressive stress as the optimal compressive stress, for example, the optimal compressive stress $S_k$: 15 MPa.

Ninth step: While the fixed slenderness ratio of the fiber is the same as that in the first step and i=0, set an initial volume content of the fiber $P_i=0\%$, and determine an addition increment $\Delta P$ of the fiber. When an added fiber is a coarse fiber, an addition increment of the fiber is $\Delta P=0.50\%$. When an added fiber is a fine fiber, an addition increment of the fiber is $\Delta P=0.05\%$; $P_{i+1}=P_i+\Delta P$.

Tenth step: Pressurize to the preset compressive stress $S_k$, after the compressive stress is stabilized, maintain a compression amount, continuously pressurize for about 2 minutes, stop pressurizing, immediately removing an outer mold, remove an inner mold after waiting for 24 hours, taking out a specimen from a curing room after standard curing for 28 days, and perform a uniaxial compression test on the specimen by using a 3,000 KN MTS compression test apparatus. In a test process, a measurement system is used to measure an axial deformation of the specimen. The measurement system includes four linear variable displacement transducers (LVDTs) that are at right angles to each other and fastened on an aluminum frame and has a measuring length of 185 mm. In addition, four horizontal strain gauges are used to measure the transverse strain of the specimen. To record an applied load and deformation well, all specimens in the present disclosure are tested in a loading mode of performing force control and then performing displacement control. A loading system of the mode is with a loading rate for force control is 1 KN/s, and when a force reaches 5 KN, perform displacement control, with a loading rate of the displacement control of 0.3 mm/min and a data acquisition rate of 1 Hz. Finally, calculate the average toughness of three specimens in the same group, and denote the average toughness as $T_i$, if $T_i < T_{i-1}$, perform twelfth step, or if $T_i \geq T_{i-1}$, perform eleventh step.

Eleventh step: Increase the content of the fiber to $P_i+\Delta P$, i=i+1, and perform ninth step.

Figure 3:
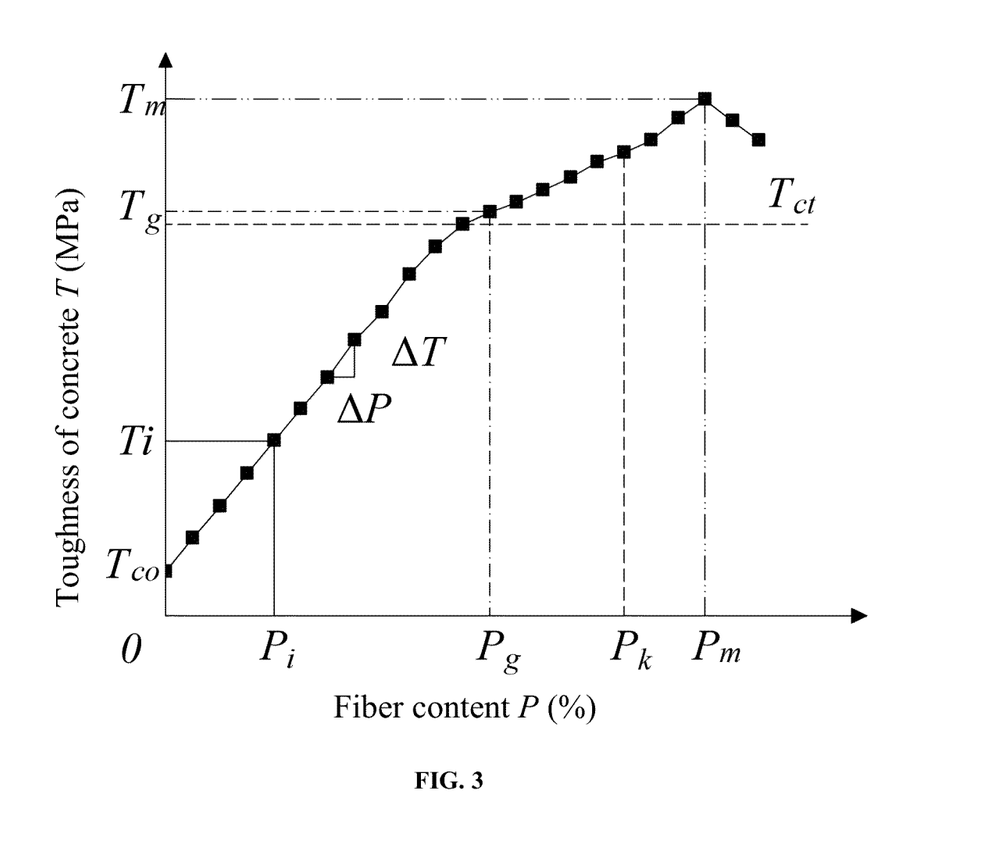
FIG. 3 is a schematic diagram of a relationship between fiber content and the average toughness of CCFRC.

Twelfth step: Draw a relationship curve of toughness $T_i$ and a fiber content P of the CCFRC (i=0, 1, 2, ..., n). When toughness $T_g$ is greater than and closest to a designed $T_{cr}$, a fiber content $P_g$ corresponding to the toughness $T_g$ is the minimum content within the optimal range, and a fiber content Pm corresponding to toughness $T_m$ at the highest point of the curve is the maximum content of the fiber within the optimal range, as shown in FIG. 3.

Thirteenth step: Perform one to two series of experiments with the same concrete material and mix proportion, repeat ninth step to twelfth step until that $P_g$ and $P_m$ convergences (within an allowable range of an error) are obtained, if a minimum content result and a maximum content result of the fiber obtained based on the curve are the same as those in twelfth step, determine the results, or if a minimum content result and a maximum content result of the fiber obtained based on the curve are not the same as those in twelfth step, repeat ninth step to thirteenth step until that a repeatable result is obtained.

The step of determining an optimal range of a fiber slenderness ratio in this embodiment includes the following steps.

Eighth step: On the basis of the optimal ranges of the fiber content determined in second step to seventh step, select and fix an integer pressure stress $S_k$ within the optimal range of the compressive stress as the optimal compressive stress, for example, the optimal compressive stress $S_k$: 15 MPa.

Ninth step: While the content of the fiber is the same as that in the first step and e=0, set an initial slenderness ratio of the fiber $\lambda_e=0$, and set an increment $\Delta\lambda=(l_e-l_{e-1})/d$, i.e. $\lambda_{e+1}=\lambda_e+\Delta\lambda$, where l represents a length of the fiber, and d represents a diameter of the fiber.

Tenth step: Pressurize to the preset compressive stress $S_k$, and compress the fresh concrete to a standard height of about 300 mm, after the compressive stress is stabilized, maintain a compression amount, continuously pressurize for about 2 minutes, stop pressurizing, immediately removing an outer mold, remove an inner mold after waiting for 24 hours, taking out a specimen from a curing room after standard curing for 28 days, and perform a uniaxial compression test on the specimen by using a 3,000 KN MTS compression test apparatus. In a test process, a measurement system is used to measure an axial deformation of the specimen. The measurement system includes four linear variable displacement transducers (LVDTs) that are at right angles to each other and fastened on an aluminum frame and has a measuring length of 185 mm. In addition, four horizontal strain gauges are used to measure the transverse strain of the specimen. To record an applied load and deformation well, all specimens in the present disclosure are tested in a loading mode of performing force control and then performing displacement control. To record an applied load and deformation well, all specimens in the present disclosure are tested in a loading mode of performing force control and then performing displacement control. A loading system of the mode is with a loading rate for force control is 1 KN/s, and when a force reaches 5 KN, perform displacement control, with a loading rate of the displacement control of 0.3 mm/min and a data acquisition rate of 1 Hz. Finally, calculate the average toughness of three specimens in the same group, and denote the average toughness as $T_e$, if $T_e<T_{e-1}$, perform twelfth step, or if $T_e \geq T_{e-1}$, perform eleventh step.

Eleventh step: Increase the slenderness ratio of the fiber to $\lambda_e+\Delta\lambda$, e=e+1, and return to step 15.

Figure 4:
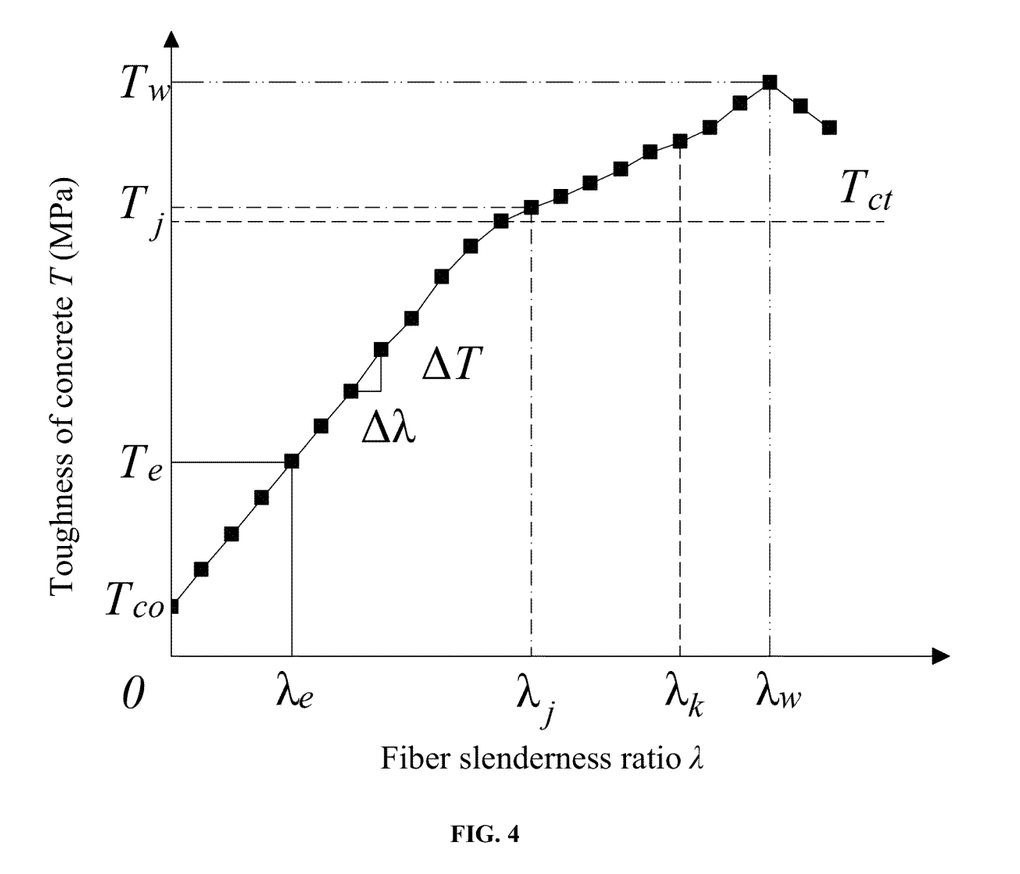
FIG. 4 is a schematic diagram of a relationship between a fiber slenderness ratio and the average toughness of CCFRC.
Figure 5:
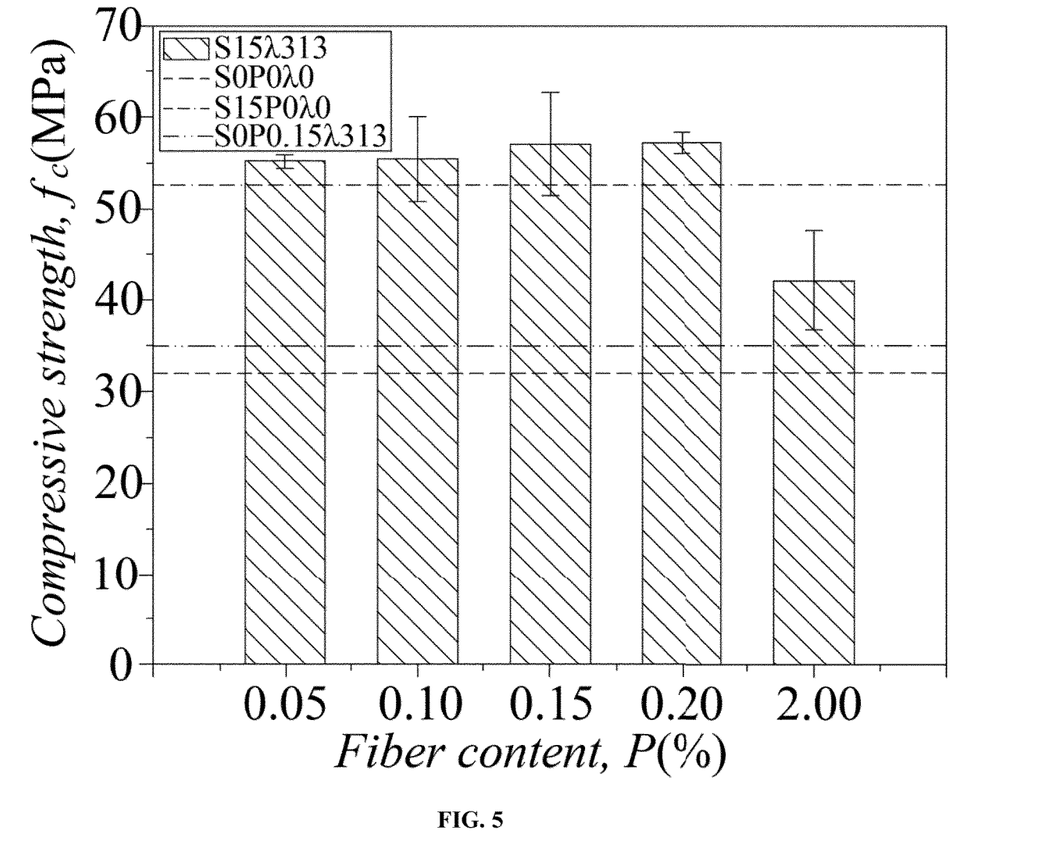
FIG. 5 is a schematic diagram of the average strength of plain concrete, compressed plain concrete, plain fiber-reinforced concrete, and CCFRC with different fiber admixtures.
Figure 6:
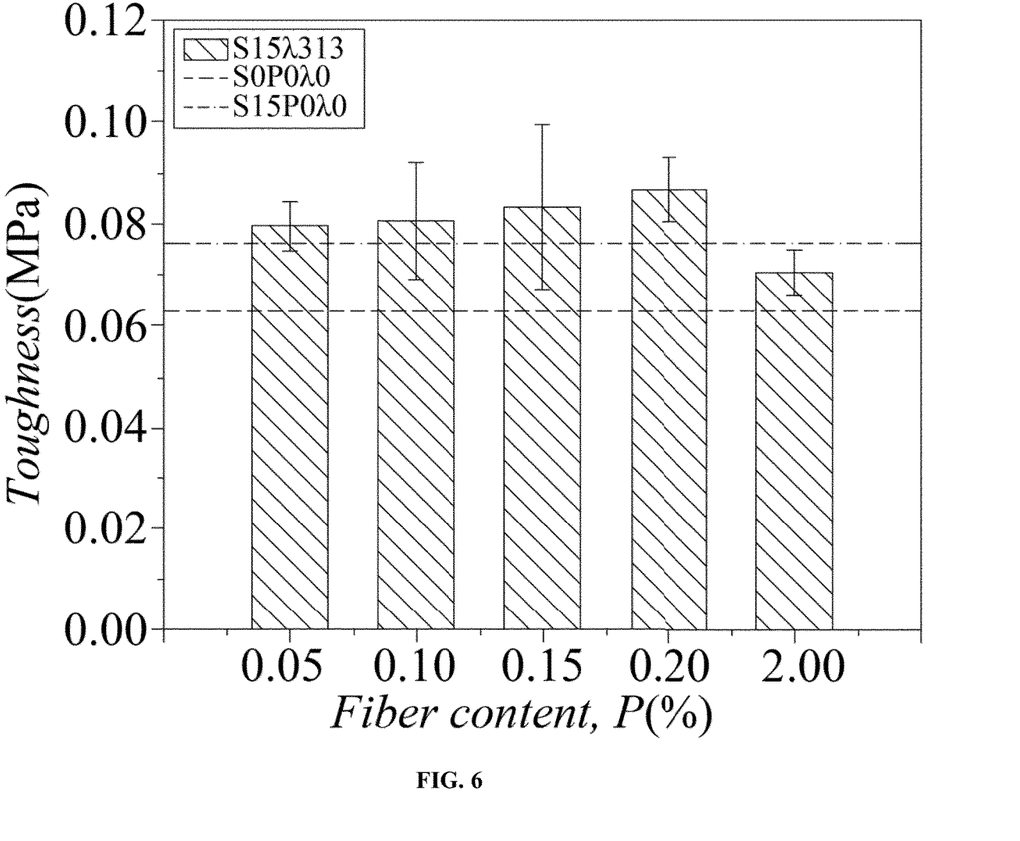
FIG. 6 is a schematic diagram of the average toughness of ordinary concrete, compressed ordinary concrete, and CCFRC with different fiber content.
Figure 7:
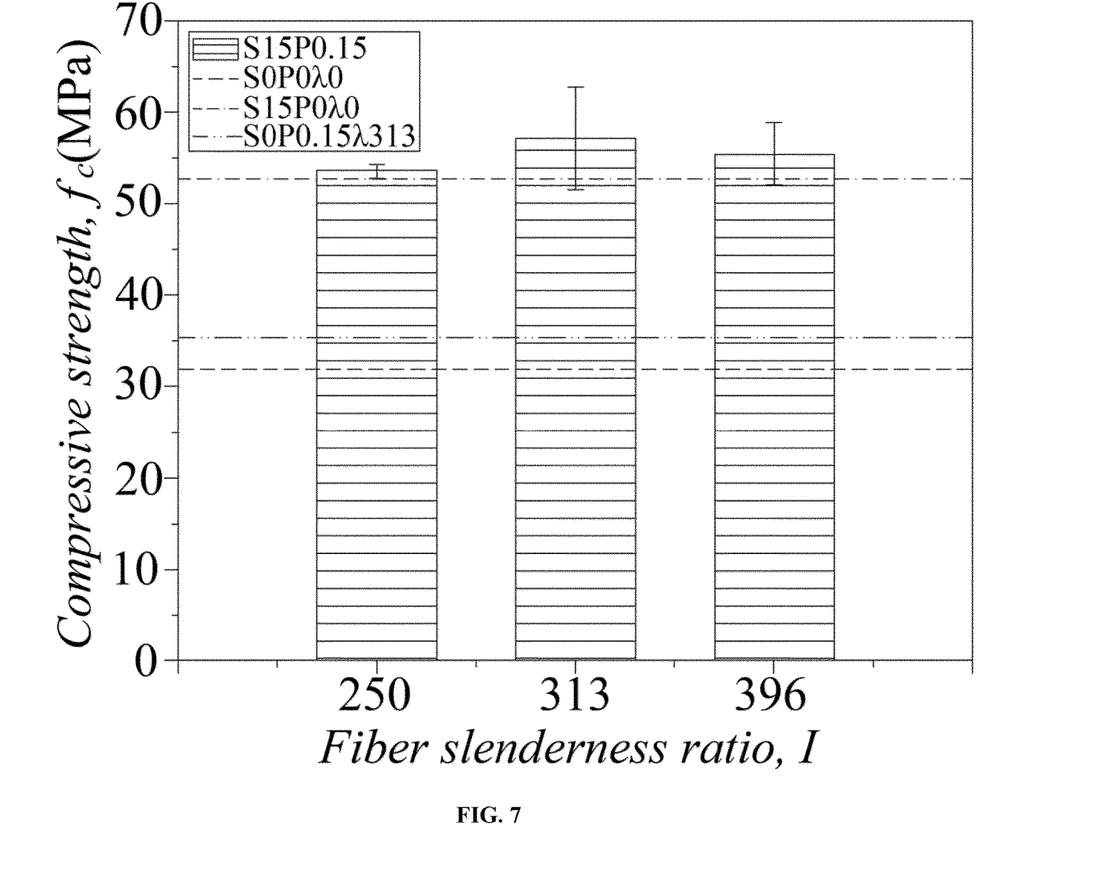
FIG. 7 is a schematic diagram of the average strength of ordinary concrete, compressed ordinary concrete, ordinary fiber-reinforced concrete, and CCFRC with a different fiber slenderness ratio.
Figure 8:
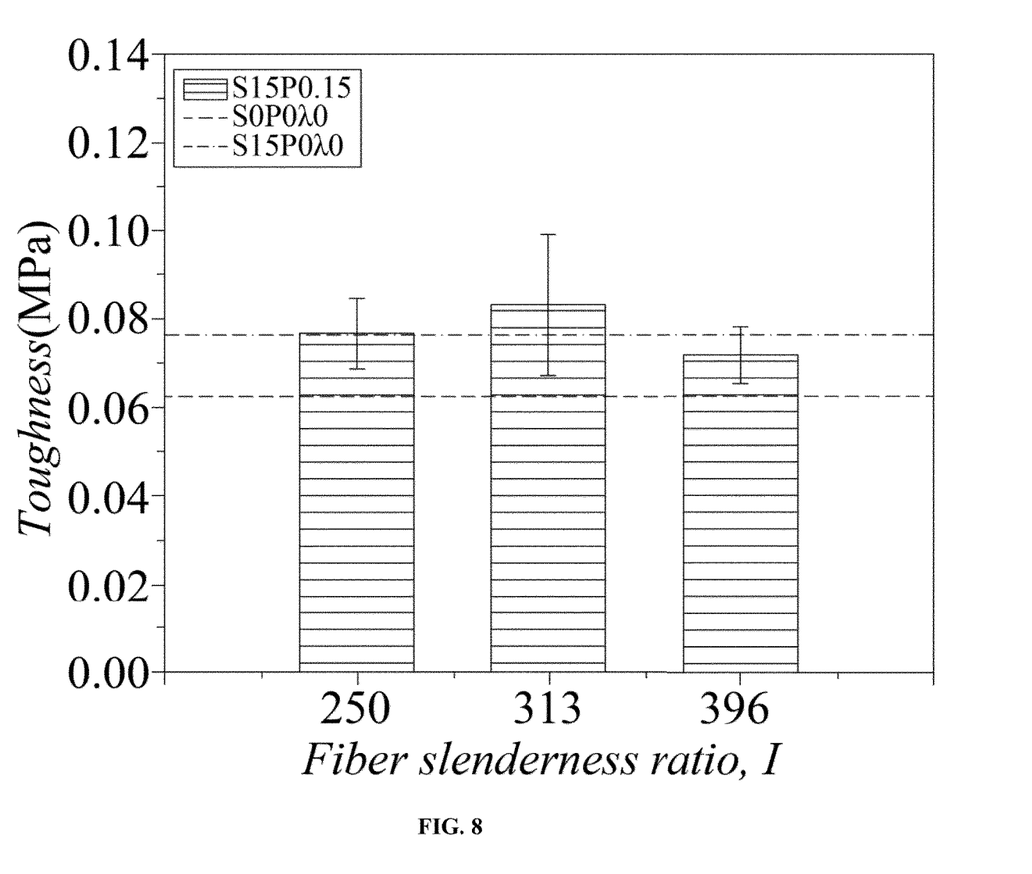
FIG. 8 is a schematic diagram of the average toughness of ordinary concrete, compressed ordinary concrete, and CCFRC with a different fiber slenderness ratio.

Twelfth step: Draw a relationship curve of toughness $T_e$ and a fiber slenderness ratio $\lambda$ of the CCFRC (e=0, 1, 2, . . . , n). When toughness $T_j$ is greater than and closest to a designed $T_{ct}$, a fiber slenderness ratio $\lambda_j$ corresponding to the toughness $T_j$ is the minimum slenderness ratio within the optimal range, and a fiber slenderness ratio $\lambda_w$ corresponding to toughness $T_w$ at the highest point of the curve is the maximum slenderness ratio within the optimal range, as shown in FIG. 4.

Thirteenth step: Perform one to two series of experiments with the same concrete material and mix proportion, repeat ninth step to twelfth step until that $\lambda_j$ and $\lambda_w$ convergences (within an allowable range of an error), if a minimum slenderness ratio result and a maximum slenderness ratio result of the fiber are the same as those in twelfth step, determine the results, or if are confirmed, if a minimum slenderness ratio result and a maximum slenderness ratio result of the fiber are not the same as those in twelfth step, repeat ninth step to thirteenth step until a repeatable result is obtained, to finally obtain the optimal ranges of the content and slenderness ratio of the fiber in the CCFRC.

Embodiment 2

This embodiment is a specific practical process of the design solutions of the present disclosure. In this embodiment, C30 ordinary fiber-reinforced concrete (strength of a cylinder is 35 MPa) with a designed volume content of 0.15% and slenderness ratio of 313 a fiber and C30 fiber-free compression cast ordinary concrete (strength of a cylinder is 52 MPa) is taken as a comparative group, and natural river sand with a fineness modulus of 3.0 and crushed basalt stones with a continuous grading of 5 mm to 25 mm as coarse aggregate and fine aggregate. A fiber is of bundled mono-filament polypropylene fiber, and the main physical properties of the fiber are shown in Table 1.

Under an optimized technical condition (pressurizing for 15 MPa, keeping a pressure unchanged, and continuously pressurizing for 2 minutes) for compression casting, contents of the FB in the C30 ordinary concrete and C30 ordinary fiber-reinforced concrete are decreased and increased, contents of C, W, CA, and FA are kept unchanged, a slenderness ratio of the FB is decreased or increased, and the contents of the C, W, CA, and FA are kept unchanged. A compressive strength test is performed on a concrete specimen that is cured for 28 days, and a relationship between the content and slenderness ratio of the fiber and the compressive strength is evaluated, to obtain a fiber content and fiber slenderness ratio that may significantly improve mechanical property of the CCFRC.

TABLE 1

| Main physical properties of polypropylene fiber | | | | | | | | |
|---|---|---|---|---|---|---|---|---|
| Fiber type | Length (mm) | Diameter (μm) | Slenderness ratio | Section | Modulus of elasticity (GPa) | Tensile strength (MPa) | Density (g/cm³) | Elongation at break (%) |
| Polypropylene fiber | 12 | 48 | 250 | Round | 4.7 | 450 | 0.90 | 35 |
| | 15 | | 313 | | | | | |
| | 19 | | 396 | | | | | |

TABLE 2

Mix proportion of ordinary concrete

| Grade of concrete | Stone (kg/m³) | Water (kg/m³) | P.O 42.5 cement (kg/m³) | Sand (kg/m³) | Water-cement ratio (w/c) |
|---|---|---|---|---|---|
| C30[a] | 1078 | 245 | 481 | 606 | 0.51 |

[a]C30 means the compressive strength of concrete is 30 MPa

TABLE 3

Mix proportion of CCFRC with different content and slenderness ratio of fiber

| Specimen | Stone (kg/m³) | Water (kg/m³) | Cement (kg/m³) | Sand (kg/m³) | w/c | Content of fiber (%) | Slenderness ratio of fiber | Ordinary concrete specimen (pcs) | Strength after 28 days (MPa) | CCFRC specimen (pcs) | Cylinder strength after 28 days (MPa) |
|---|---|---|---|---|---|---|---|---|---|---|---|
| 1 | 1078 | 245 | 481 | 606 | 0.51 | 0 | 0 | 3 | 32.32 31.73 32.14 | 3 | 49.45 52.14 56.98 |
| 2 | 1078 | 245 | 481 | 606 | 0.51 | 0.05 | 313 | — | — | 3 | 59.01 55.71 54.87 |
| 3 | 1078 | 245 | 481 | 606 | 0.51 | 0.10 | 313 | — | — | 3 | 56.21 54.63 51.23 |
| 4 | 1078 | 245 | 481 | 606 | 0.51 | 0.15 | 313 | 3 | 36.99 34.35 34.47 | 3 | 53.50 61.12 56.94 |
| 5 | 1078 | 245 | 481 | 606 | 0.51 | 0.20 | 313 | — | — | 3 | 56.72 57.95 57.43 |
| 6 | 1078 | 245 | 481 | 606 | 0.51 | 2.00 | 313 | — | — | 3 | 45.04 42.03 39.55 |
| 7 | 1078 | 245 | 481 | 606 | 0.51 | 0.15 | 250 | — | — | 3 | 54.45 54.65 51.59 |
| 8 | 1078 | 245 | 481 | 606 | 0.51 | 0.15 | 396 | — | — | 3 | 51.66 57.29 53.67 |

Table 1, Table 2, and Table 3 show test data of a 150 mm×300 mm concrete cylinder that is completed in the present disclosure, including physical and mechanical properties of the fiber, a mix proportion of the ordinary concrete, a mix proportion of the CCFRC with different content and slenderness ratio of the fiber, a number of specimens. The appearance and shape of a specimen of the CCFRC with different content and slenderness ratios of the fiber show that a high-quality specimen can still be produced by compression casting when the fluidity of the CCFRC is poor.

The foregoing tables show the strengths of cured concrete with different mix proportions. According to the present disclosure, the toughness of the CCFRC can be significantly improved. To see a change in the strength and toughness more clearly, in the present disclosure, FIG. 5, FIG. 6, FIG. 7, and FIG. 8 are introduced. FIG. 5, FIG. 6, FIG. 7, and FIG. 8 show the average strength and average toughness of ordinary concrete, compressed ordinary concrete, ordinary fiber-reinforced concrete, and CCFRC that have different contents and slenderness ratios of the fiber after those concrete are cured for 28 days. Ranges of fiber content and fiber slenderness ratio that may significantly improve the performance and toughness of the CCFRC can be found in the foregoing tables and the accompanying drawings of the specification, and the ranges are optimal ranges of the content and slenderness ratio of the fiber in the CCFRC.

In the description of the present disclosure, it should be noted that orientations or position relationships indicated by terms "center", "top", "bottom", "left", "right", "vertical", "horizontal", "inner", "outer" and the like are based on the orientation or position relationships as shown in the drawings, for ease of describing the present disclosure and simplifying the description only, rather than indicating or implying that the indicated device or element must have a particular orientation or be constructed and operated in a particular orientation. Therefore, these terms should not be understood as a limitation of the present disclosure. Moreover, the terms such as "first" and "second" are used herein only for the purpose of description and can-not be construed as indicating or implying relative importance.

Specific examples are used for illustration of the principles and implementations of the present disclosure. The description of the above embodiments is merely used to help understand the method and its core ideas of the present disclosure. In addition, those of ordinary skill in the art can make modifications in terms of specific implementations and scope of use according to the ideas of the present disclosure. In conclusion, the content of this specification shall not be construed as a limitation to the present disclosure.

What is claimed is:

1. A method for determining an optimal fiber content and fiber slenderness ratio in compression-cast fiber-reinforced concrete (CCFRC), comprising the following steps:

step 1, selecting and fixing a fiber content and fiber slenderness ratio that meets a specification requirement; setting a first compressive stress, a pressurization amount, and a pressurizing time; pouring fresh concrete into a mold, and controlling, based on the first compressive stress and the pressurizing time, a pressurizing structure to apply a pressure on the concrete, to obtain a first average compressive strength of the concrete; determining a second compressive stress of the concrete based on the pressurization amount and the first compressive stress, pouring the fresh concrete into the mold, and controlling, based on the second compressive stress and the pressurizing time, the pressurizing structure to apply a pressure to the concrete, to obtain a second average compressive strength of the concrete, and by analogy to obtain an $N^{th}$ average compressive strength, wherein in the process, a compressive stress that is correspondingly applied each time is gradually increased based on the pressurization amount, and when the $N^{th}$ average compressive strength is less than an $(N-1)^{th}$ average compressive strength, stopping increasing the compressive stress, drawing a relationship curve of a compressive strength and the compressive stress of the CCFRC, and determining an optimal range of the compressive stress of the CCFRC;

step 2, taking a fixed value within the optimal range of the compressive stress of the CCFRC in step 1 as an acceptable optimal compressive stress; applying the optimal compressive stress to the fresh concrete by compression casting, maintaining the optimal compressive stress for a specific period of time, and performing a uniaxial compression test after demolding and curing for a preset number of days, to obtain a mechanical property of the CCFRC under the optimal compressive stress;

step 3, keeping the slenderness ratio of the fiber in step 1 and the optimal compressive stress in step 2 unchanged, decreasing or increasing the content of the fiber, keeping a content of another material unchanged, repeating step 2 to obtain a mechanical property of CCFRC with a different content of the fiber under the optimal compressive stress, drawing a relationship curve of average toughness and the content of the fiber in the CCFRC, to statistically determine an optimal range of the content of the fiber;

step 4, keeping the content of the fiber in step 1 and the optimal compressive stress in step 2 unchanged, decreasing or increasing the slenderness ratio of the fiber, keeping the content of another material unchanged, and repeating step 2 to obtain a mechanical property of CCFRC with a different slenderness ratio under the optimal compressive stress, drawing a relationship curve of average toughness and the slenderness ratio of the fiber in the CCFRC, to statistically determine an optimal range of the slenderness ratio of the fiber;

wherein step 1 comprises:

first step, in the premise of meeting a national specification and standard, selecting and fixing a content and slenderness ratio of the fiber, determining a mix proportion of the CCFRC, and selecting a raw material required for preparation of the CCFRC, comprising a coarse aggregate, a fine aggregate, fiber, and cement;

second step, in the premise of meeting a loading capacity of current compression casting equipment, setting an initial pre-compressive stress $S_x=0$, an initial step x=0, and an increment $\Delta S$ of a compressive stress applied each time;

third step, preparing the CCFRC mixture, pouring the CCFRC mixture into the mold, pressurizing the CCFRC mixture to preset compressive stress by the pressurizing structure, removing an outer mold after maintaining the preset compressive stress for a first preset time, removing an inner mold after a second preset time, performing the uniaxial compression test on a specimen after standard curing of the CCFRC mixture for a third preset time, calculating an average compressive strength of three specimens in a same group, and denoting the average compressive strength as $f_x$; if $f_x<f_{x-1}$, performing the fifth step; or if $f_x \geq f_{x-1}$, performing the fourth step;

fourth step, increasing the pre-compressive stress to $S_x+\Delta S_x=x+1$, and performing the second step;

fifth step, obtaining a relationship curve of the average compressive strength $f_x$ and the pre-applied compressive stress $S_x$ of the CCFRC, wherein x=0, 1, 2, . . . , n, determining a minimum value and a maximum value within the optimal range of the compressive stress based on the curve, wherein $f_o=f_{co}$ represents a compressive strength of ordinary concrete, a compressive strength $f_{ct}$ represents a designed minimum compressive strength of the CCFRC, when a compressive strength fa is greater than and closest to a designed compressive strength $f_{ct}$, a compressive stress $S_a$ corresponding to the compressive strength $f_a$ is the minimum compressive stress in the optimal range, a compressive stress strength $S_h$ corresponding to a compressive strength $f_h$ at a highest point is the maximum compressive stress in the optimal range, and when determining the selected content and slenderness ratio of the fiber in the first step, determining the optimal range of the compressive stress of the CCFRC;

sixth step, repeating the second step to the fifth step with the same concrete material and mix proportion, in the premise that a content and slenderness ratio of the fiber is the same as those in the first step, if the optimal range of the compressive stress of the CCFRC is the same as that in the fifth step, determining a result, or if the optimum compressive stress range for the CCFRC is not the same as in the fifth step, repeat the second step to the sixth step until repeatable results are obtained;

the step of determining an optimal range of a content of the fiber comprises:

seventh step, on the basis of the optimal range of the compressive stress determined in the sixth step, selecting and fixing an integer compressive stress $S_k$ within the range as the acceptable optimal compressive stress;

eighth step, while the fixed slenderness ratio of the fiber is the same as that in the first step and i=0, setting an initial content of the fiber $P_i=0\%$, and determining an addition increment $\Delta P$ of the fiber;

ninth step, preparing the CCFRC mixture, pouring the CCFRC mixture into the mold, pressurizing the CCFRC mixture by the pressurizing structure to $S_k$, removing an outer mold after maintaining the preset compressive stress for a first preset time, removing an inner mold after a second preset time, performing the uniaxial compression test on a specimen after standard curing of the CCFRC mixture for a third preset time, calculating average toughness of three specimens in a same group, and denoting the average toughness as $T_i$, if $T_i<T_{i-1}$, performing the eleventh step, or if $T_i \geq T_{i-1}$, performing the tenth step;

tenth step, increasing the content of the fiber to $P_i+\Delta P$, i=i+1, and performing the eighth step;

eleventh step, in the premise that the fixed slenderness ratio of the fiber is the same as that in the first step, obtaining a relationship curve of average toughness $T_i$ and the content of the fiber in the CCFRC under optimal compressive stress $S_k$, wherein i=0, 1, 2, . . . , n, determining a minimum value and a maximum value within an optimal range of the content of the fiber based on the curve, wherein $T_o=T_{co}$ represents toughness of ordinary concrete, and toughness $T_{ct}$ represents designed minimum toughness of the CCFRC, when toughness $T_g$ is greater than and closest to a designed toughness $T_{ct}$, a content $P_g$ of the fiber corresponding to the toughness $T_g$ is the minimum content within the optimal range, and a content $P_m$ of the fiber corresponding to toughness $T_m$ at the highest point of the curve is the maximum content within the optimal range; and twelfth step, repeating the eighth step to the eleventh step with the same concrete material and mix proportion, if the minimum content and the maximum content of the fiber is within the optimal range and that is obtained based on the relationship curve of average toughness and the content of the fiber in the CCFRC are the same as those in the eleventh step, determining a result, or if the minimum content and the maximum content of the fiber that are within the optimal range and that are obtained based on the relationship curve of average toughness and the content of the fiber in the CCFRC are not the same as that in the eleventh step, repeating the eighth step to the twelfth step until that a reproducible result is obtained;

the step of an optimal range of a slenderness ratio of the fiber comprises:

seventh step, on the basis of the optimal range of the compressive stress determined in the sixth step, selecting and fixing the integer compressive stress $S_k$ within the range as the optimal compressive stress;

eighth step, while the content of the fiber is the same as that in the first step and e=0, setting an initial slenderness ratio of the fiber $\lambda_e$=0, and setting an increment $\Delta\lambda=(l_e-l_{e-1})/d$, wherein l represents a length of the fiber, and d represents a diameter of the fiber;

ninth step, preparing the CCFRC mixture, pouring the CCFRC mixture into the mold, pressurizing the CCFRC mixture by the pressurizing structure to $S_k$, and removing an outer mold after maintaining the preset compressive stress for a first preset time, removing an inner mold after a second preset time, performing the uniaxial compression test on a specimen after standard curing of the CCFRC mixture for a third preset time, calculating average toughness of three specimens in a same group, and denoting the average toughness as $T_e$, if $T_e < T_{e-1}$, performing the eleventh step, or if $T_e \geq T_{e-1}$, performing the tenth step;

tenth step, increasing the slenderness ratio of the fiber to $\lambda_e+\Delta\lambda$, e=e+1, and performing eighth step;

eleventh step, in the premise that the content of the fiber is the same as that in the first step, obtaining a relationship curve of average toughness $T_e$ and the slenderness ratio of the fiber in the CCFRC under the optimal compressive stress $S_k$, wherein e=0, 1, 2, ..., n, determining a minimum value and a maximum value within the optimal range of the slenderness ratio of the fiber based on the curve, wherein $T_o=T_{co}$ represents toughness of ordinary concrete, and toughness $T_{ct}$ represents designed minimum toughness of the CCFRC, when toughness $T_j$ is greater than and closest to a designed toughness $T_{ct}$, a slenderness ratio $\lambda_j$ of the fiber corresponding to the toughness $T_j$ is the minimum slenderness ratio within the optimal range, and a slenderness ratio $\lambda_w$ corresponding to toughness $T_w$ at the highest point of the curve is the maximum slenderness ratio within the optimal range;

twelfth step, repeating the eighth step to the eleventh step with the same concrete material and mix proportion, if the minimum value and the maximum value within the optimal range of the slenderness ratio of the fiber that are obtained based on the relationship curve of average toughness and the content of the fiber in the CCFRC are the same as those in the eleventh step, determining a result, or if the minimum value and the maximum value within the optimal range of the slenderness ratio of the fiber that are obtained based on the relationship curve of average toughness and the content of the fiber in the CCFRC are not the same as those in the eleventh step, repeating the eighth step to the twelfth step until that a reproducible result is obtained; and finally determining ranges of an optimal content and slenderness ratio of the fiber to be added to the CCFRC under the optimal compressive stress.

2. The method for determining an optimal fiber content and fiber slenderness ratio in CCFRC according to claim 1, wherein the increment $\Delta S$ of compressive stress applied each time is 1 MPa to 2 MPa.

3. The method for determining an optimal fiber content and fiber slenderness ratio in CCFRC according to claim 1, wherein after the specimen taken out from a curing room, first, an end part that is compressed by a jack head is ground by using a grinding machine, to enable a surface to be flat and smooth, second, the uniaxial compression test is performed on the specimen by using a compression test apparatus, wherein a loading system is to perform force control first and then perform displacement control, with a loading rate of the force control of 1 KN/s, and when a force reaches 5 KN, displacement control is performed at a loading rate of the displacement control of 0.3 mm/min; in a testing process, for longitudinal strain of the specimen, a deformation of the specimen needs to be measured by using a measuring system with a measuring length of 185 mm; and for transverse strain of the specimen, measurement needs to be performed by using four strain gauges that are horizontally arranged with a length of 50AA, and a data acquisition rate is 1 hz.

4. The method for determining an optimal fiber content and fiber slenderness ratio in CCFRC according to claim 1, wherein when an added fiber is coarse fiber, the addition increment of the fiber is $\Delta P=0.50\%$, or when an added fiber is fine fiber, the addition increment of the fiber is $\Delta P=0.05\%$.

5. The method for determining an optimal fiber content and fiber slenderness ratio in CCFRC according to claim 1, wherein after the compressive stress is stabilized, the compression amount is maintained, pressurization is continuously performed for 2 minutes, the outer mold is immediately removed, the inner mold is removed after 24 hours, the specimen is taken out from the curing room after standard curing for 28 days, and the uniaxial compression test is performed.

* * * * *